United States Patent
Bartels et al.

(10) Patent No.: US 7,822,476 B2
(45) Date of Patent: Oct. 26, 2010

(54) ELECTRODE LINE AND TERMINAL PART FOR AN IMPLANTABLE HEART STIMULATOR

(75) Inventors: Klaus Bartels, Berlin (DE); Carsten Steglich, Berlin (DE); Thomas Guenther, Michendorf (DE)

(73) Assignee: Biotronik CRM Patent AG, Baar (CH)

( * ) Notice: Subject to any disclaimer, the term of this patent is extended or adjusted under 35 U.S.C. 154(b) by 273 days.

(21) Appl. No.: 12/022,706

(22) Filed: Jan. 30, 2008

(65) Prior Publication Data

US 2008/0188919 A1   Aug. 7, 2008

(30) Foreign Application Priority Data

Feb. 7, 2007   (DE) .................. 10 2007 006 089

(51) Int. Cl.
*A61N 1/372* (2006.01)
(52) U.S. Cl. ........................................ 607/36
(58) Field of Classification Search ............. 607/36–38; 439/909
See application file for complete search history.

(56) References Cited

U.S. PATENT DOCUMENTS 5,304,219 A * 4/1994 Chernoff et al. ............ 607/122
7,326,083 B2 * 2/2008 Mehdizadeh et al. ... 439/607.12
2005/0221671 A1 * 10/2005 Lyu et al. .................... 439/587
2007/0027517 A1 * 2/2007 Bischoff et al. ............. 607/122

OTHER PUBLICATIONS

German Search Report, dated Oct. 4, 2007.

* cited by examiner

*Primary Examiner*—George R Evanisko
*Assistant Examiner*—Hiba El-Kaissi
(74) *Attorney, Agent, or Firm*—ARC IP Law, PC; Joseph J. Mayo

(57) ABSTRACT

A terminal part for an electrode line for connection to an implantable heart stimulator, the terminal part having multiple annular, electrically conductive contacts of equal external diameter having insulation sections of the same external diameter situated between them in the longitudinal direction, of which the electrically conductive contacts are each electrically connected to an electrically conductive terminal line, the terminal part being formed by multiple insulating adapters and by electrical contacts held thereby having terminal lines fastened thereon, which are plugged together and connected using a thermoplastic injection molding compound after being plugged together, the terminal part otherwise being implemented in such a way that it is to be connected as an independent unit to a remaining electrode line.

23 Claims, 5 Drawing Sheets

ELECTRODE LINE AND TERMINAL PART FOR AN IMPLANTABLE HEART STIMULATOR

This application takes priority from German Patent Application DE 10 2007 006 089.2, filed 7 Feb. 2007, the specification of which is hereby incorporated herein by reference.

BACKGROUND OF THE INVENTION

1. Field of the Invention

The present invention relates to an electrode line for connection to an implantable heart stimulator, such as a cardiac pacemaker or a cardioverter/defibrillator. In particular, the present invention relates to a terminal part for such an electrode line.

2. Description of the Related Art

Implantable heart stimulators of the type cited are fundamentally known in various embodiments. Heart stimulators of this type typically have a sealed housing, which comprises a power supply and further electronic and electrical components to generate stimulation pulses or defibrillation shocks and deliver them to one or more chambers of a heart via an electrode line or to acquire and process electrical potentials in the heart. For this purpose, such implantable heart stimulators are typically connected to electrode lines, which are plugged using a terminal part at the proximal end of the electrode line into a socket in a so-called header of the particular heart stimulator. Both the terminal part and also the socket in the header of the heart stimulator have electrical contacts corresponding to one another to produce an electrical connection between the heart stimulator and the electrode line.

Accordingly, the terminal part at the proximal end of the electrode line has electrical contacts which are connected to terminal lines, which produce at least a part of an electrical connection to stimulation and/or sensing electrodes in the area of the distal end of such electrode line. Such electrode lines are typically flexible (i.e., bending) and are known in manifold embodiments.

The terminal part relevant here is of the type which has multiple annular contacts of equal external diameter and corresponds to the future standard IS-4. A variant of a terminal part of this type is described, for example, in US 2005/0221671.

BRIEF SUMMARY OF THE INVENTION

The present invention relates to the terminal part at the proximal end of the electrode line and its connection to remaining electrode lines.

The object of the present invention is to provide a terminal part and an electrode line having such a terminal part, which are independent of the type and number of the contacts of the electrode line, are to be produced at acceptable outlay, and have high reliability.

This object is achieved according to the present invention by a terminal part and by an electrode line having a terminal part, which has multiple annular, electrically conductive contacts of equal external diameter having insulation sections of the same external diameter situated between them in the longitudinal direction, each of the electrically conductive contacts being electrically connected to one electrically conductive terminal line. The terminal part according to the present invention is formed by multiple insulating adapters and electrical contacts, retained thereby, having terminal lines fastened thereto, plugged together in the longitudinal direction of the terminal part and extrusion coated using insulating plastic after being plugged together. The terminal lines project either not at all or at most by an amount which is less than the remaining length of the terminal part beyond a distal end of the terminal part.

The adapters are preferably produced as semi-finished parts using injection molding. The injection molding compound consists of a single material, or the injection molding compound comprises PEEK, or the injection molding compound contains at least two materials, or the injection molding compound comprises PEEK and polyurethane.

Otherwise, the terminal part according to the present invention is implemented in such a way that it is to be connected to a remaining electrode line as an independent unit.

This allows the complete terminal part to be prefinished and checked before it is connected to the remaining electrode line. A faulty terminal part may thus already be identified before it is connected to the remaining electrode line. Rejection produced in case of an error on the terminal part thus does not relate to the entire electrode line.

Sprues required for the extrusion coating and absolutely necessary partition planes of injection molds are placed in such a way that an external surface of the insulating plastic has no mold marks in the area between the individual electrical contacts and proximally from the contact situated most proximally. For practical considerations, such as because of requirements which result from biocompatibility, the extrusion coating may also be performed in multiple steps using differing materials, so that a heterogeneous external structure results, which at least partially encloses the adapters.

Alternatively thereto, the adapters may be implemented and plugged together in the longitudinal direction in such a way that they form the external contour of the terminal part together with the electrical contacts and an inner chamber of the terminal part enclosed by the adapters is injection molded using insulating plastic.

In both cases, the adapters are used for securing the electrically conductive contacts in position both axially and also radially.

To ensure efficient manufacturing and increase the reliability of the terminal part, according to a preferred embodiment variant, at least two of the insulating adapters are identical to one another. This provides the further advantage that the terminal part may be constructed without further measures having one, two, or three annular contacts, without other components being necessary for this purpose.

The identical adapters preferably each have a precisely fitting seat for a particular annular contact. This means that the particular adapter has at least one external dimension in a longitudinal section which corresponds to the internal diameter of the annular contacts.

In connection with the latter embodiment variant, it is advantageous if the adapters identical to one another in a particular proximal longitudinal section have a longitudinal stop which delimits pushing on a particular annular contact in the proximal direction. The longitudinal section preferably has a longitudinal distance to a proximal end of a particular adapter which corresponds to the longitudinal distance between the annular contacts and thus defines the insulation length between the annular contacts.

In a distal longitudinal section, the adapters identical to one another preferably have a smaller external diameter than in their proximal longitudinal section. The external diameter of the distal longitudinal section is dimensioned in such a way that a particular distal longitudinal section fits precisely in a central opening in the proximal longitudinal section of an identical adapter, so that the adapters are to be plugged one inside the other in this way. By plugging the sequential adapters one inside the other, a coherent carrier for the annular contacts thus results, which requires no further carrier elements and fixes the annular contacts both radially and also axially. Therefore, the adapters allow a carrier for the contacts to be produced in a simple way, which is flexible in regard to its length and the number of contacts.

One section of the particular proximal longitudinal section of a particular adapter having its relatively large external diameter forms the seat for each particular annular contact.

The adapters preferably have at least one depression running in the longitudinal direction on their exterior side, which is used to receive a particular terminal line of an annular contact.

In addition to the adapters, the terminal part preferably has a distal terminus part, which has a proximal end section and a distal end section. Both end sections preferably have approximately the same external diameter. The proximal end section of the distal terminus part preferably corresponds to a particular proximal longitudinal section of the adapters between the proximal end of the particular adapter and the longitudinal stop, i.e., the proximal end sections of all adapters and of the distal terminus part are identical.

The distal terminus part preferably also has, in its proximal end section, at least one depression running in the longitudinal direction for receiving a terminal line of an annular contact. The distal terminus part is otherwise not implemented to receive a further annular contact, but rather to be connected to the remaining electrode line.

The plugged-together adapters and the terminus part are preferably oriented to one another in such a way that the particular depressions on the exterior side of the adapters and the terminus part align with one another and allow a particular terminal line to be led stretched and parallel to the longitudinal axis of the terminal part in the depressions. For this purpose, openings are provided in an extension of a particular depression in a transition area of the adapters between their proximal longitudinal section having greater external diameter and their distal longitudinal section having smaller external diameter, which allow a particular terminal line to penetrate this transition area of a particular adapter.

Two or three of the depressions are preferably provided distributed uniformly around the circumference in each adapter and in the distal terminus part. The depressions in the proximal longitudinal sections of greater diameter of the adapters are offset around the circumference in relation to the depressions in the distal longitudinal sections.

A further advantageous feature of a preferred terminal part is a central lumen which extends essentially through all identical adapters and also through the terminus part and may receive centrally a proximal end of an electrical line, which is coiled, for example.

In addition, a segment is provided on the proximal end of the terminal part which is inserted precisely fitting into the opening on the proximal end of the one identical adapter which is located on the proximal end of the terminal part. Various electrode line configurations having fixed and/or rotatable electrode lines may be attached to the finished terminal part via the segment, without the terminal part having to be altered.

The terminal part of the type described above is preferably a component of an electrode line which, in its distal end, has at least one electrode and additionally at least one electrical supply line, which is electrically connected at its distal end to this electrode and is electrically connected at its proximal end to a terminal line of an annular contact of the terminal part via a crimped, welded, or soldered connection.

The crimped, welded, or soldered connection is preferably located in one of the depressions of the distal terminus part of the terminal part running in the longitudinal direction. Because the distal terminus part itself comprises insulating plastic and the individual electrical supply lines and terminal lines are electrically insulated from one another by the various depressions in the terminus part, no further insulation of the connection point is necessary even after the connection of the particular terminal line to the associated electrical supply line.

As already indicated above, the electrode line preferably additionally has a helically coiled (coil-shaped) line, which extends between the distal and proximal ends of the electrode line and has a proximal line end section extending into the lumen of the terminal part.

It is submitted that various preferred features of the terminal part and/or the electrode line mentioned above and cited in the dependent claims may be combined with one another.

BRIEF DESCRIPTION OF THE DRAWINGS

An electrode line corresponding to the above statements will be explained in greater detail on the basis of an exemplary embodiment with reference to the figures. In the figures.

DETAILED DESCRIPTION OF THE INVENTION

Figure 1:
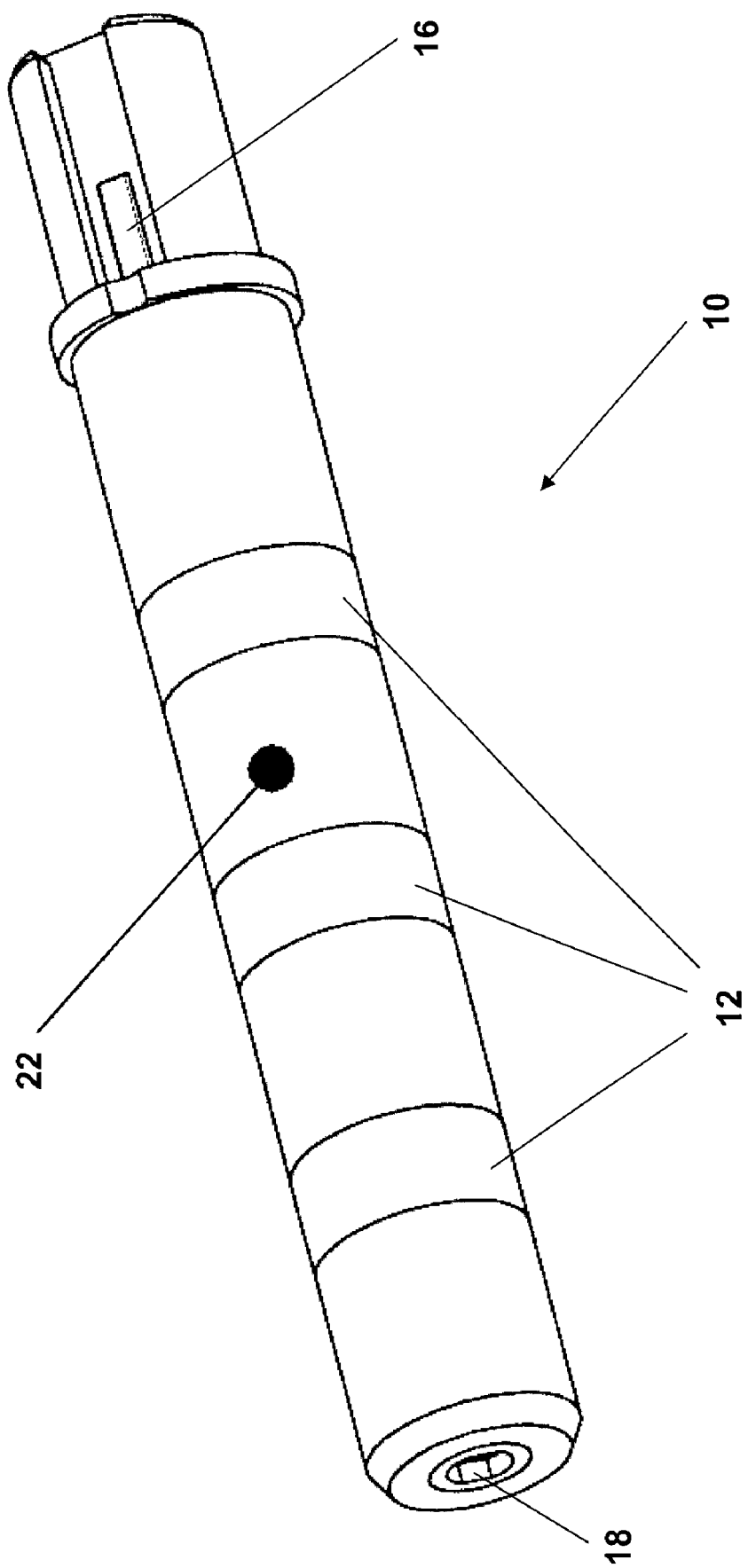
FIG. 1: shows a terminal part manufactured as a separate unit in a perspective external view.

The terminal part 10 shown in FIG. 1 has three annular contacts 12, which are situated on a carrier formed by adapters 14 (not recognizable further in FIG. 1). The annular contacts 12 are each provided with terminal lines 16, which end proximally from a distal end of the terminal part 10 (the right end of the terminal part 10 in FIG. 1). A key face 18 which is part of a key segment 20 (see FIG. 2) is located at the proximal end of the terminal part 10. The terminal part 10 is extrusion coated using insulating plastic, which forms insulation faces 22 between blank, electrically conductive external faces of annular contacts 12.

Figure 2:
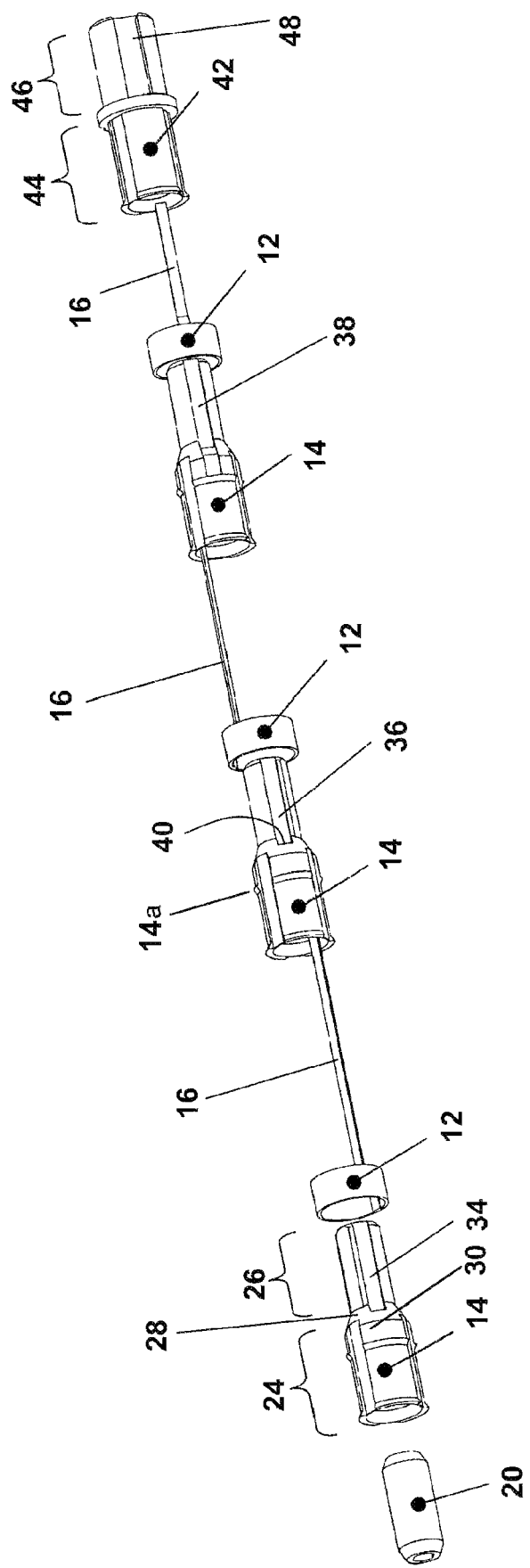
FIG. 2: shows an exploded drawing of the terminal part from FIG. 1 having an illustration of the individual components.

The components of the terminal part 10 are shown individually in an exploded drawing in FIG. 2. A total of three annular contacts 12 having terminal lines 16 fastened thereto are provided. Because the annular contacts 12, as shown in FIG. 1, are offset to one another in the longitudinal direction of the terminal part 10, the terminal lines 16 of the individual annular contacts 12 are of different lengths and thus have an equal distance to the distal end of the terminal part 10 on their particular distal end.

Each of the annular contact elements 12 is carried by a particular adapter 14. A total of three adapters 14 are provided, which are identical to one another. Each of the adapters 14 has a proximal longitudinal section 24 and a distal longitudinal section 26 and a transition area 28 situated in between. A part of the proximal longitudinal section 24 of a particular adapter 14 is used as a seat 30 for a particular annular contact 12. A longitudinal stop 14a, which has a specific distance to the distal end of a particular adapter 14, defines the seat 30 for the annular electrodes 12 in the longitudinal direction of the particular proximal longitudinal section 24 of a particular adapter 12.

The particular distal longitudinal sections 26 of a particular adapter 14 have a smaller diameter than the proximal longitudinal sections 24, which is dimensioned in such a way that a particular distal longitudinal section 26 is to be inserted precisely fitting in a central opening in the proximal longitudinal section 24 of an identical adapter 14. In this way, multiple adapters 14 may be connected to one another in the longitudinal direction. The external diameter of the adapter is reduced in the transition area 28 between the two longitudinal sections of a particular adapter 14.

Depressions 34, 36, and 38 running in the longitudinal direction are provided on the exterior side of the longitudinal sections 24 and 26 of the adapters 14. These depressions 34, 36, and 38 are used for receiving a particular terminal line 16 of an annular contact 12. The depressions 34, 36, and 38 are situated in such a way that a terminal line 16 of a particular contact 12 is led from the exterior side of a particular proximal longitudinal section of the corresponding adapter 14 in a depression (in this case the depression 38 in each case) to the exterior side of the distal longitudinal section 26 of the particular adapter 14. To be able to lead each of the terminal lines 16 into proximity to the distal end of the terminal part 10, the remaining depressions 36 on a particular distal longitudinal section 26 of an adapter 14 are situated in an extension of an opening 40 in the transition area 28 of a particular adapter 14. The openings 40 allow a particular depression 38 to continue in the linear direction in corresponding aligned depressions 36 of one or more further distally situated adapters 14.

A terminus part 42, which has a proximal end section 44 and a distal end section 46, is situated on the distal end of the terminal part 10. The proximal end section 44 is shaped similarly to the proximal longitudinal sections 24 of the adapters 14, but has no seat for a further annular electrode. The distal end section 46 of the terminus part 42 has approximately the same external diameter as the proximal end section 44 of the terminus part 42 and also has depressions 48 running in the longitudinal direction. As shown in FIG. 1, each of the terminal lines 16 end in one of these depressions 48 when the terminal part 10 is completely assembled. The ends of the terminal lines 16 are externally accessible in the depressions 48.

Figure 3:
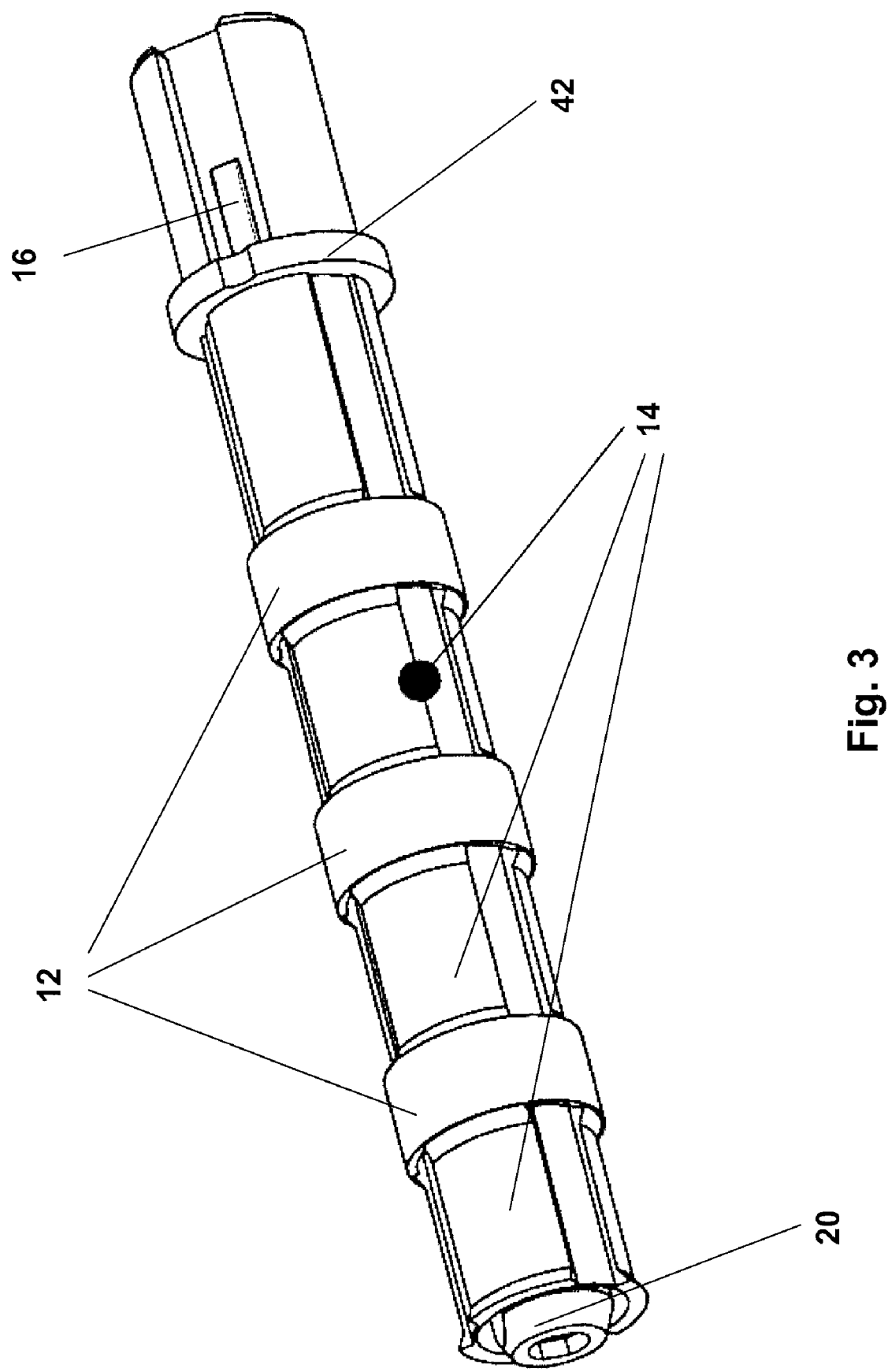
FIG. 3: shows the plugged-together components of the terminal part from FIG. 1 before the extrusion coating.

As already noted, the adapters 14 and the terminus part 42 may be plugged into one another in the longitudinal direction and form a contact carrier for the electrical contacts 12 in this way. FIG. 3 shows a plugged-together adapter that form terminal part 10 before the extrusion coating using insulating plastic.

Figure 4:
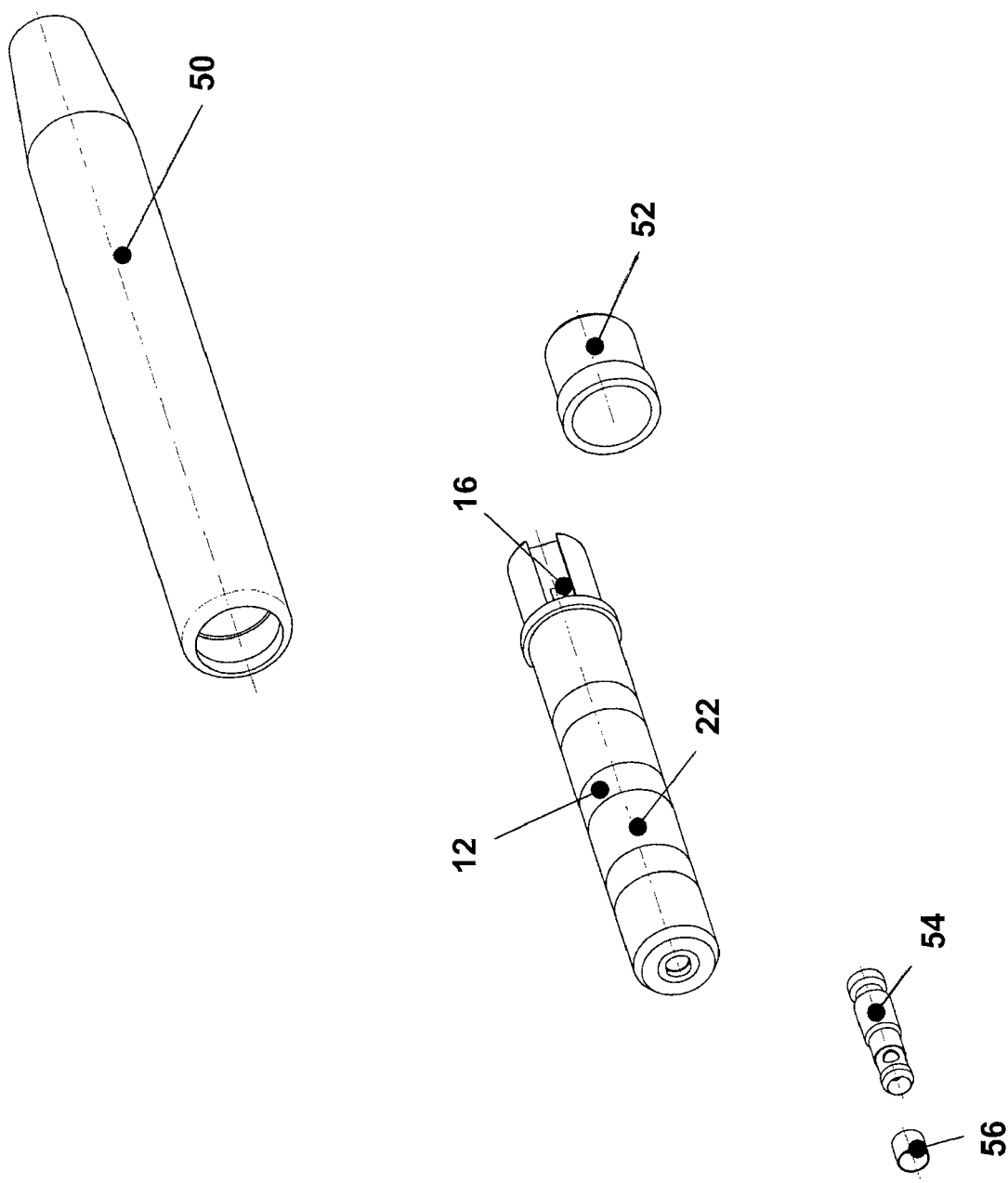
FIG. 4: shows the terminal part from FIG. 1 with further components for connecting the terminal part of a remaining electrode line.

To be able to connect the finished terminal part 10 to a remaining electrode line, further parts are required, which are shown in FIG. 4. These are a silicone sleeve 50, a terminus ring 52, a plug pin 54, and a marking band 56.

Figure 5:
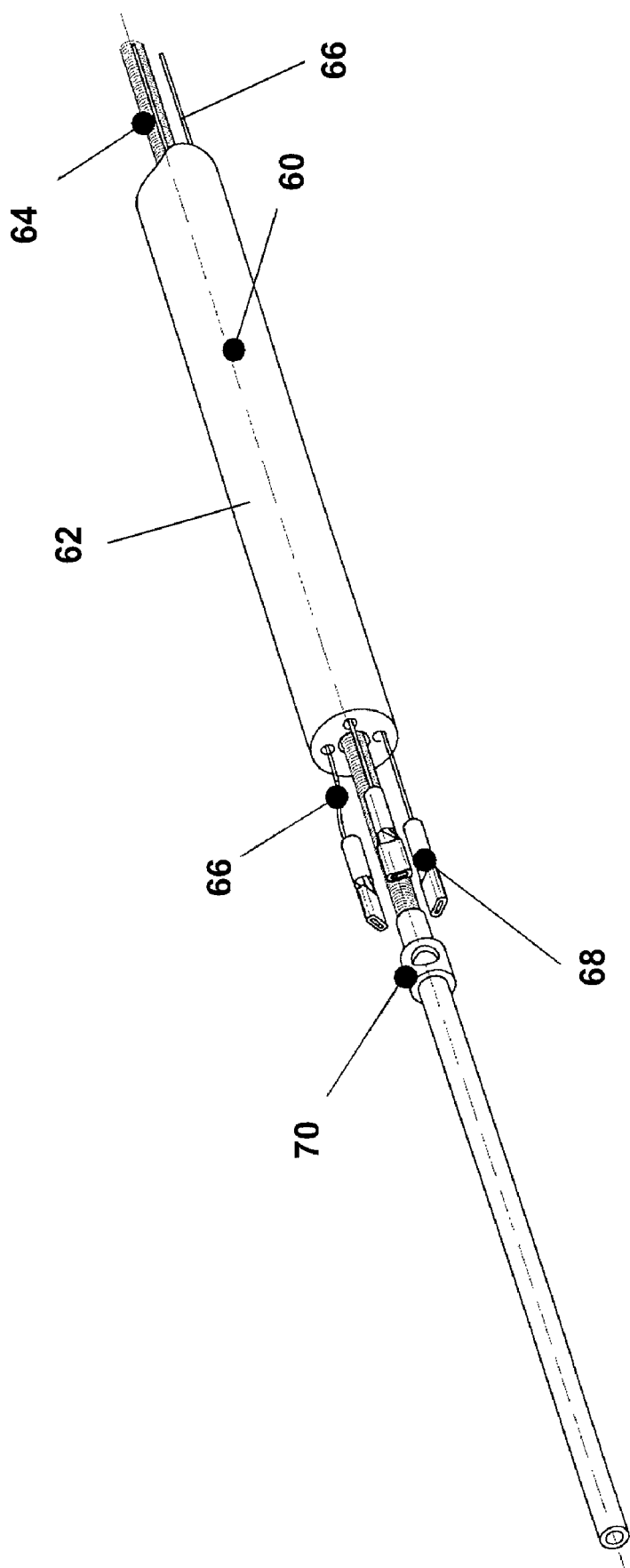
FIG. 5: shows a remaining electrode line which is preconfigured for connection to the terminal part from FIGS. 1 through 4.

With the aid of the latter components, the terminal part 10 may be connected to a proximal end of a preconfigured electrode line 60, as shown in FIG. 5. FIG. 5 only shows the proximal end of such a preconfigured electrode line 60. As shown in FIG. 5, the electrode line 60 has a flexible envelope 62, which has a central lumen for a central, helically coiled supply line 64, and further externally situated lumens for electrical supply lines 66. The electrical supply lines 66 are each equipped with a crimp sleeve 68 on their particular proximal end, which is used for connecting the electrical supply lines 66 to the terminal lines 16 of the annular electrodes 12. A sleeve 70 is fastened to the proximal end of the helically coiled line 64, which extends through a continuous central lumen of the terminal part 10 enclosed by the terminus part 42 and the adapters 14 when the terminal part 10 is fastened to the electrode line 60. A proximal end of the sleeve 70 is then connected to the plug pin 54. The plug pin 54 then forms a central contact for the helically coiled line 64.

The following mounting steps are thus required to connect the finished terminal part 10 to the electrode line 60. Firstly, the crimp sleeves 68 are fastened to the ends of the supply lines 66 by crimping. Subsequently, the sleeve 70 is bonded by laser welding to the proximal end of the helically coiled line 64. The prepared proximal end of the electrode line 60 shown in FIG. 5 is then inserted into the terminal part 10 and fixed to the plug pin 54. The silicone sleeve 50 and the terminus ring 52 are then brought over the transition points as connection elements. The marking band 56 covers a fusion edge for the laser welded bond between the plug pin 54 and the sleeve 70.

This description of a preferred exemplary embodiment makes it clear that the terminal part 10 may be extensively manufactured and checked already before its connection to an electrode line 60, so that it is ensured that the terminal part 10 is error-free when it is connected to the electrode line 60. This reduces the rejection rate and increases the quality of the finished electrode line.

What is claimed is

1. A terminal part for an electrode line for connection to an implantable cardiac stimulator and/or implantable defibrillator comprising:
    multiple hollow adapters having proximal longitudinal sections and distal longitudinal sections respectively;
    multiple insulation faces;
    multiple annular, electrically conductive contacts of equal external diameter wherein said multiple insulation faces of said equal external diameter are situated between said multiple annular, electrically conductive contacts in a longitudinal direction;
    multiple electrically conductive terminal lines of different lengths;
    wherein each of the electrically conductive contacts are electrically connected to a respective one of said multiple electrically conductive terminal lines;
    a terminus part having depressions on an outer portion of a distal longitudinal portion of said terminus part wherein said depressions are aligned in said longitudinal direction and offset inward toward a centerline of said terminus part wherein said terminus part is hollow and configured to couple with a distal longitudinal section of one of said multiple hollow adapters that is placed within a proximal portion of said terminus part that is hollow and wherein said terminus part is a most distal element that forms said terminal part;
    wherein said multiple insulation faces comprise an injection molding compound that surrounds each of said proximal longitudinal sections of each of said multiple hollow adapters;
    wherein said multiple annular, electrically conductive contacts are coupled between said multiple insulation faces;
    wherein said multiple electrically conductive terminal lines are situated in said depressions and wherein each of said multiple electrically conductive terminal lines of different lengths terminates at a respective one of said depressions in said terminus part and wherein each of said multiple electrically conductive terminal lines of different lengths terminates at a substantially same longitudinal distance along said terminus part and wherein said multiple electrically conductive terminal lines of different lengths do not extend beyond said terminus part; and, wherein said terminal part is configured to connect to an electrode line as an independent unit at said terminus part.

2. The terminal part according to claim 1, wherein said terminal part further comprises an interior and an external contour and wherein the distal longitudinal sections of said multiple hollow adapters are situated in said interior of the terminal part, and said external contour of the terminal part comprises the injection molding compound together with the electrically conductive contacts.

3. The terminal part according to claim 1, further comprising an inner chamber, wherein the multiple insulation faces form an external contour of the terminal part together with the electrically conductive contacts and enclose said inner chamber that comprises the injection molding compound.

4. The terminal part according to one of claim 1, wherein the multiple electrically conductive terminal lines end proximally from the distal end of the terminus.

5. The terminal part according to claim 1, wherein the injection molding compound consists of a single material.

6. The terminal part according to claim 5, wherein the injection molding compound comprises PEEK.

7. The terminal part according to claim 1, wherein the injection molding compound contains at least two materials.

8. The terminal part according to claim 7, wherein the injection molding compound comprises PEEK and polyurethane.

9. The terminal part according to claim 1, wherein at least some of the multiple hollow adapters are identical to one another.

10. The terminal part according to claim 1, wherein the multiple hollow adapters identical to one another each have a precisely fitting seat for a particular annular contact.

11. The terminal part according to claim 10, wherein the multiple hollow adapters identical to one another have a longitudinal stop in a proximal longitudinal section, which delimits a length of travel of a particular one of said multiple annular, electrically conductive contacts in a proximal direction.

12. The terminal part according to claim 11, wherein the longitudinal stop has a longitudinal distance to a proximal end of a particular one of the multiple hollow adapters wherein the longitudinal distance also defines an insulation length between the multiple annular, electrically conductive contacts.

13. The terminal part according to claim 10, wherein the multiple hollow adapters have a smaller external diameter in a distal longitudinal section than in their proximal longitudinal section, wherein an external diameter in the distal longitudinal section is configured so that a particular distal longitudinal section fits precisely in a central opening in the proximal longitudinal section of another identical adapter, so that the multiple hollow adapters are configured to be plugged one inside another and thus connected to one another.

14. The terminal part according to claim 13, wherein the proximal longitudinal section of a particular adapter comprises a seat situated at a relatively larger external diameter portion of a particular annular contact.

15. The terminal part according to claim 13, wherein the multiple hollow adapters have at least one depression running in the longitudinal direction on their exterior side that is configured to receive a terminal line selected from said multiple electrically conductive terminal lines, wherein said terminal line is associated with an annular contact.

16. The terminal part according to claim 15, wherein the adapters identical to one another have a transition area between their particular proximal longitudinal section and their distal longitudinal section, in which the external diameter decreases and which has an opening in extension of a particular depression, which leads from an exterior of the distal longitudinal section into an interior of the proximal longitudinal section.

17. The terminal part according to claim 1, wherein the terminus part, which has a proximal end section and a distal end section, both have approximately equal external diameters and of which the proximal end section of the distal terminus part corresponds to a particular proximal longitudinal section of the multiple hollow adapters between the proximal end of the particular adapter and the longitudinal stop of particular adapter.

18. The terminal part according to claim 15, wherein each of the multiple hollow adapters and the terminus part have, around the circumference of their longitudinal sections and/ or the distal longitudinal section, three depressions distributed uniformly around the particular circumference that are configured to receive a total of three terminal lines selected from said multiple electrically conductive terminal lines wherein said three terminal lines are associated with three annular contacts, which are oriented to one another in such a way that they each align in the longitudinal direction.

19. The terminal part according to claim 1, wherein the terminal part has a central, free lumen extending over its entire length.

20. The terminal part according to claim 1, wherein the terminal part has a form fitting segment which is inserted precisely fitting into an opening at the proximal end of that of the identical adapters which is located at a proximal end of the terminal part.

21. The terminal part according to claim 1, as a component of an electrode line, which has at least one electrode and at least one electrical supply line at its distal end, which is electrically connected to this electrode, wherein the electrical supply line is electrically connected to a terminal line of an annular contact via a crimped, welded, or soldered connection.

22. The electrode line according to claim 21, wherein the crimped, welded, or solder connection is situated in one of the depressions running in the longitudinal direction on an exterior side of the distal end section of a distal terminus part.

23. The electrode line according to claim 19, wherein the electrode line has a coiled line extending between its distal and its proximal ends, which extends into a lumen of the terminal part using a proximal line end section.

* * * * *